US007396658B2

(12) United States Patent
Haupert, Jr.

(10) Patent No.: US 7,396,658 B2
(45) Date of Patent: Jul. 8, 2008

(54) METHODS FOR SCREENING HIF LIKE OUABAIN-RESISTANT NA$^+$—K$^+$-ATPASE AGENTS

(75) Inventor: Garner T. Haupert, Jr., Littleton, MA (US)

(73) Assignee: The General Hospital Corporation, Boston, MA (US)

(*) Notice: Subject to any disclaimer, the term of this patent is extended or adjusted under 35 U.S.C. 154(b) by 389 days.

(21) Appl. No.: 10/803,185

(22) Filed: Mar. 16, 2004

(65) Prior Publication Data

US 2004/0248080 A1 Dec. 9, 2004

Related U.S. Application Data

(62) Division of application No. 09/220,913, filed on Dec. 24, 1998, now Pat. No. 6,846,646.

(51) Int. Cl.
*C12Q 1/42* (2006.01)
*C07H 19/20* (2006.01)
*C07H 19/207* (2006.01)

(52) U.S. Cl. .............................. 435/21; 435/4; 435/7.91; 536/26.13; 536/26.24

(58) Field of Classification Search .................... 435/4, 435/21, 7.91; 536/26.13, 26.24
See application file for complete search history.

(56) References Cited

U.S. PATENT DOCUMENTS

| | | | |
|---|---|---|---|
| 5,716,937 | A | 2/1998 | Haupert, Jr. |
| 5,910,484 | A | 6/1999 | Haupert, Jr. |
| 6,265,383 | B1 | 7/2001 | Haupert, Jr. |
| 6,846,646 | B1 | 1/2005 | Haupert, Jr. |
| 6,998,470 | B1 | 2/2006 | Gallagher et al. |
| 2004/0248080 | A1 | 12/2004 | Haupert, Jr. |

FOREIGN PATENT DOCUMENTS

| | | |
|---|---|---|
| WO | WO 98/53832 | 12/1988 |
| WO | WO 97/19099 | 5/1997 |
| WO | WO 98/07739 A1 | 2/1998 |
| WO | WO 98/53831 A1 | 12/1998 |
| WO | WO 98/53832 | 12/1998 |
| WO | WO 98/54195 A1 | 12/1998 |
| WO | WO 00/11017 | 3/2000 |
| WO | WO 00/39328 A1 | 7/2000 |
| WO | WO 01/25281 A1 | 4/2001 |
| WO | WO 2004/000328 A1 | 12/2003 |

OTHER PUBLICATIONS

Anner, B.M., et al., "Right-Side-Out Pumping Na, K-ATPase-Liposomes: A New Tool to Study the Enzyme's Receptor Function," *Biophys. Res. Commun.*, 129:102-108 (1985).
Anner, B.M., et al., "Hypothalamic Na$^+$-K$^+$-ATPase Inhibitor Characterized in Two-Sided Liposomes Containing Pure Renal Na$^+$-K$^+$-ATPase," *Am. J. Physiol.*, 258:F144-F153 (1990).
Carilli, et al., "Hypothalmic factor inhibits the (Na, K) ATPase from the extracellular surface," *J. Biol. Chem.*, 260:1027-1031 (1985).
Crabos, et al., "Atrial natriuretic peptide regulates release of Na$^+$-K$^+$-ATPase inhibitor from rat brain," *Am. J. Physiol.*, 254:F912-F917 (1988).
Croyle, M.L., et al., "Extensive Random Mutagenesis Analysis of the Na$^+$/K$^+$-ATPase α Subunit Identifies Known and Previously Unidentified Amino Acid Residues that Alter Ouabain Sensitivity," *Eur. J. Biochem.*, 248(2):488-495 (1997).
De Angelis, C., et al., "Hypoxia Triggers Release of an Endogenous Inhibitor of Na$^+$-K$^+$-ATPase from Midbrain and Adrenal," *Am. J. Physiol.*, 274:F182-F188 (1998).
Decollogne, et al., "Biochemical characterization of the Na$^+$/K$^+$-ATPase isoforms in human heart," The Sodium Pump, Bamberg and Schoner (eds) pp. 812-815 (1994).
Doucet, et al., "Determination of Na-K-ATPase activity in single segments of the mammalian nephron," *Am. J. Physiol.*, 237(2):F105-F113 (1979).
Ferrandi, M., et al., "Ouabainlike Factor in Milan Hypertensive Rats," *Am. J. Physiol.*, 263:F739-F748 (1992).
Haupert, G., et al., "Hypothalamic sodium-transport inhibitor is a high-affinity reversible inhibitor of Na$^+$-K$^+$-ATPase," *Am. J. Physiol.*, 247:F919-F924 (1984).
Haupert, G.T., "Structure and Biological Activity of the Na$^+$/K$^+$-ATPase Inhibitor Isolated from Bovine Hypothalamus: Difference from Ouabain," The Sodium Pump, Bamberg and Schoner (eds), Steinkopff & Darmstadt (pub), N.Y., pp. 732-742 (1994).
Holzinger, et al., "Molecular basis for the insensitivity of the Monarch (Danaus plexippus) to cardiac glycosides," *FEBS* 314:477-480 (1992).
Jaisser, et al., "Primary sequence and functional expression of a novel ouabain-resistant Na, K-ATPase," *J. Biol. Chem.* 267:16895-16903 (1992).
Janssens, S.P., et al., "Hypothalamic Na$^+$, K$^+$-ATPase Inhibitor Constricts Pulmonary Arteries of Spontaneously Hyperactive Rats," *Journal of Cardiovascular Pharmacology*, 22(Suppl. 2), S42-S46 (1993).

(Continued)

*Primary Examiner*—Chih-Min Kam
(74) *Attorney, Agent, or Firm*—Medlen & Carroll, LLP

(57) ABSTRACT

The present invention relates to rapid, quantitative, specific, high through-put methods for screening test substances for their ability to inhibit activity of an ouabain-resistant Na$^+$—K$^+$-ATPase involved in a variety of biological processes such as regulation of osmotic balance and cell volume, maintenance of the resting membrane potential, establishment of the ionic composition of cerebrospinal fluid and aqueous humor, electrical activity of muscle and nerve, and receptor-mediated endocytosis, cardiac muscle contractility, neurotransmitter metabolism and vascular muscle cell contraction. These methods can be employed to identify compounds for use in therapeutic applications for disease processes in which dysfunction of the Na$^+$—K$^+$-ATPase contributes to a pathological process. The present invention also includes kits which are used in the methods provided herein. The present invention further includes methods of treating or preventing diseases or disorders which are associated with dysfunction of the Na$^+$—K$^+$—ATPase.

16 Claims, No Drawings

OTHER PUBLICATIONS

Levenson, R., "Isoforms of the Na, K-ATPase: Family Members in Search of Function," *Rev. Physiol. Biochem. Pharmacol.*, 123:1-45 (1994).

Lingrel, J.B., et al., "Na, K-ATPase: Cardiac Glycoside Binding and Functional Importance of Negatively Charged Amino Acids of Transmembrane Regions," The Sodium Pump (Bamberg and Schoner, Ed.) pp. 276-286 (1994).

Sancho, J.M., et al., "A Non-Ouabain Na/K ATPase Inhibitor Isolated from Bovine Hyopthalamus. Its Relation to Hypothalamic Ouabain," *Clin. and Exper. Hypertension*, 20(5&6):535-542 (1998).

Shull, et al., "Molecular cloning of three distinct forms of the $Na^+$, $K^+$-ATPase α-subunit from rat brain," *Biochemistry*, 25:8125-8132 (1986).

Shyjan, et al., "Antisera specific for the α1, α2, α3, and β subunits of the Na, K-ATPase: Differential Expression of α and β subunits in rat tissue membranes," *Biochemistry*, 28:4531-4535 (1989).

Sweadner, Kathleen J., "Isozymes of the $Na^+/K^+$-ATPase," *Biochem. Biophys. Acta.*, 988:185-220 (1989).

Sweadner, J., "Enzymatic propeties of separated isozymes of the Na, K-ATPase," *J. Biol. Chem.*, 260:11508-11513 (1985).

Tymiak, et al., "Physicochemical characterization of a ouabain isomer isolated from bovine hypothalamus," *Proc. Natl. Acad. Sci. USA*, 90:8189-8193 (1993).

Zhao, et al., "Na, K-ATPase inhibitors from bovine hypothalamus and human plasma are different from ouabain: Nanogram scale CD structural analysis," *Biochem.* 34(31):9893-9896 (1995).

METHODS FOR SCREENING HIF LIKE OUABAIN-RESISTANT NA$^+$—K$^+$-ATPASE AGENTS

RELATED APPLICATION(S)

This application is a divisional of U.S. application Ser. No. 09/220,913, filed Dec. 24, 1998, now U.S. Pat. No. 6,846,646.
The entire teachings of the above application(s) are incorporated herein by reference.

GOVERNMENT SUPPORT

The invention was supported, in whole or in part, by a grant, R01 HL52282, from the National Heart, Lung and Blood Institute of the National Institutes of Health. The Government has certain rights in the invention.

BACKGROUND OF THE INVENTION

Na$^+$—K$^+$-ATPASE is a plasma membrane-associated enzyme which is encoded by a multigene family. Activity of the Na$^+$—K$^+$-ATPase provides gradients of Na$^+$ and K$^+$ that are essential for maintaining cellular homeostasis. (Levenson, Rev. *Physiol. Biochem. Pharmacol.* 123:1-45, 1994). The ion gradients established by the Na$^+$—K$^+$-ATPase play a central role in regulating osmotic balance, cell volume, and maintaining the resting membrane potential. Na$^+$-coupled transport of nutrients, establishment of the ionic composition of cerebrospinal fluid and aqueous humor, electrical activity of muscle and nerve, and receptor-mediated endocytosis are all processes which depend on the activity of the enzyme.

Compounds have been identified that inhibit Na$^+$—K$^+$-ATPase, and at least some of these compounds, plant-derived cardiac glycosides like ouabain and digoxin, have found therapeutic utility, such as treatment of congestive heart failure. However, ouabain can also have deleterious side effects that have not been associated with the use of an endogenous compound, hypothalamic inhibitory factor (HIF), which also has been found to have an inhibitory effect on Na$^+$—K$^+$-ATPase.

Sensitivity of the Na$^+$—K$^+$-ATPase to ouabain and HIF lies within the α subunit of the enzyme. To date, all α2 and α3 isoforms and α1 isoforms from most mammals and other organisms tested are sensitive to ouabain, i.e., can be inhibited at relatively low ouabain concentrations. However, certain α1 isoforms are resistant to ouabain.

A need exists to identify other inhibitors of Na$^+$—K$^+$-ATPase which, like HIF, will have fewer potential side-effects than ouabain, and related cardiac glycosides obtained from plants.

SUMMARY OF THE INVENTION

The present invention is directed to methods and kits for screening a test substance for HIF inhibitory activity of an ouabain-resistant Na$^+$—K$^+$-ATPase and for treating or preventing diseases or disorders with substances identified by the screening methods described herein.

In one embodiment, the method includes contacting an ouabain-resistant Na$^+$-K$^+$-ATPase with a test substance under conditions suitable for measuring or detecting ouabain-resistant Na$^+$—K$^+$-ATPase activity. The ouabain-resistant Na$^+$—K$^+$-ATPase inhibitory activity of the test substance is measured or detected. The level of activity of the ouabain-resistant Na$^+$—K$^+$-ATPase measured or detected in the presence of the test substance is then compared with the ouabain-resistant Na$^+$—K$^+$-ATPase activity measured or detected in the presence of HIF under comparable conditions, thereby determining whether the test substance exhibits HIF inhibitory activity.

In another embodiment, the method includes contacting the ouabain-resistant Na$^+$—K$^+$-ATPase with a test substance in the presence of ATP and a non-ATP substrate, under conditions suitable for measuring or detecting ouabain-resistant Na$^+$—K$^+$-ATPase activity. Oxidation of the non-ATP substrate is measured or detected to determine the ATPase activity. This activity is compared to the activity measured or detected using again the oxidation of a non-ATP substrate contacted with ouabain-resistant Na$^+$—K$^+$-ATPase and ATP in the presence of HIF under comparable conditions, thereby determining whether the test substance exhibits HIF inhibitory activity.

In still another embodiment, the method includes contacting ouabain-resistant Na$^+$—K$^+$-ATPase with a test substance in the presence of ATP, wherein the terminal phosphate ($P_3$) is labeled, under conditions suitable for measuring or detecting liberated labeled $P_3$. Labeled $P_3$ liberated from the ATP substrate is measured or detected. The measured or detected liberated labeled $P_3$ is compared with measured or detected labeled $P_3$ liberated by contact of ouabain-resistant Na$^+$—K$^+$-ATPase with HIF in the presence of ATP, wherein the terminal phosphate is labeled, and under comparable conditions, thereby determining whether the test substance exhibits HIF activity.

In a further embodiment, a liposome containing, or a cell containing or expressing, ouabain-resistant Na$^+$—K$^+$-ATPase is contacted with a test substance in the presence of a compound comprising Rb$^+$, under conditions suitable for isotopic Rb$^+$ uptake by the liposomes or the cells. The amount of isotopic Rb$^+$ present in the liposomes or cells is compared with isotopic Rb$^+$ measured or detected in liposomes or cells obtained by contacting liposomes containing, or cells containing or expressing, ouabain-resistant Na$^+$—K$^+$-ATPase with HIF in the presence of a compound comprising isotopic Rb$^+$, under comparable conditions, thereby determining whether the test substance exhibits HIF inhibitory activity.

A kit of the invention includes an isolated ouabain-resistant Na$^+$—K$^+$-ATPase, or reconstituted liposomes or cells containing or expressing, an ouabain-resistant Na$^+$—K$^+$-ATPase. The kit also includes HIF, a non-ATP substrate, ATP or labeled ATP, and a compound containing isotopic Rb$^+$.

In another embodiment, the kit includes an isolated ouabain-resistant Na$^+$—K$^+$-ATPase, ATP, NADH and HIF.

In a further embodiment, the kit includes an isolated ouabain-resistant Na$^+$—K$^+$-ATPase, ATP in which the $P_3$ is labeled and HIF.

In yet another embodiment, the kit includes reconstituted liposomes containing, or cells containing or expressing, ouabain-resistant Na$^+$—K$^+$-ATPase, a compound containing isotopic Rb$^+$ and HIF.

A method of the invention treats or prevents a disease or disorder by administering, to a subject to whom such treatment or prevention is in need thereof, an effective therapeutic amount of a biologically active substance identified by any of the methods described herein for screening a test substance as exhibiting HIF inhibitory activity.

The present invention encompasses rapid, quantitative, specific, high through-put methods for screening test substances such as drugs, ligands (natural or synthetic), ligand antagonists, peptides, small organic molecules and the like, for their ability to inhibit activity of an ouabain-resistant Na$^+$—K$^+$-ATPase involved in a variety of biological processes. Examples of such biological processes include the regulation of osmotic balance and cell volume, maintenance of the resting membrane potential, establishment of the ionic composition of cerebrospinal fluid and aqueous humor, electrical activity of muscle and nerve, and receptor-mediated endocytosis, cardiac muscle contractility, neurotransmitter metabolism and vascular muscle cell contraction. Identification of other substances that, like HIF, inhibit ouabain-resistant $Na^+$—$K^+$-ATPase, may lead to treatment or prevention of disorders or diseases without the side effects characteristic of ouabain.

DETAILED DESCRIPTION OF THE INVENTION

The features and other details of the invention will now be more particularly described and pointed out below and in the claims. It will be understood that the particular embodiments of the invention are shown by way of illustration and not as limitations of the invention. The principle features of this invention can be employed in various embodiments without departing from the scope of the invention.

The present invention is directed to methods and kits for screening a test substance for HIF inhibitory activity of an ouabain-resistant $Na^+$—$K^+$-ATPase and for treating or preventing diseases or disorders with substances identified by the screening methods described herein. It is believed that other compounds which, like HIF, inhibit ouabain-resistant $Na^+$—$K^+$-ATPase may also share a low toxicity profile.

Sensitivity of $Na^+$—$K^+$-ATPase to ouabain and hypothalamic inhibitory factor (HIF) lies within the $\alpha$ subunit of the enzyme. However, certain $\alpha_1$ isoforms isolated from rats, mice, species of amphibians such as the toad Bufo marinus, and species of butterflies such as the Monarch butterfly Danaus plexippus, are resistant to ouabain (Levenson R., Rev. Physiol. Biochem. Pharmacol., 123:1-45, 1994; Holzinger et al., FEBS 314:477-480, 1992; and Jaisser et al., J. Biol. Chem. 267:16895-16903, 1992). In order to inhibit these ouabain-resistant $Na^+$—$K^+$-ATPases, a 100 fold or higher concentration of ouabain than that capable of inhibiting ouabain sensitive $Na^+$—$K^+$-ATPase generally is needed. In addition, a number of mutations have been found to be able to convert an ouabain-sensitive $Na^+$—$K^+$-ATPase into an ouabain-resistant one (Lingrel et al., The Sodium Pump (Bamberg and Schoner, Ed.) pp. 276-286, 1994). Most of these mutations are located within the extracellular domains or at the borders of the extracellular domains. While inactivation of the ouabain-resistant $\alpha_1$ isoform (obtained from rat kidney) requires concentrations of ouabain $10^2$-$10^3$ greater than that for inactivating the ouabain-sensitive $\alpha_2/\alpha_3$ isoforms (obtained from rat brain axolemma) (Sweadner, Biochem. Biophys. Acta. 988: 185-220, 1989), such is not the case for hypothalamic inhibitory factor (hereinafter HIF). Ferrandi and co-workers isolated HIF from bovine and rat hypothalamus (Ferrandi et al., Am. J. Physiol. 263:F739-F748, 1992), and discovered that HIF could inhibit ouabain-resistant $Na^+$—$K^+$-ATPase at physiological dosages.

In one embodiment of the present invention, an ouabain-resistant $Na^+$—$K^+$-ATPase is contacted with a test substance under suitable conditions. An example of a suitable medium is an aqueous medium for which the ouabain-resistant $Na^+$—$K^+$-ATPase is active (Sweadner, K., J. Biol. Chem., 260: 11508-11513, 1985).

Ouabain-resistant $Na^+$—$K^+$-ATPase proteins and nucleic acids can be obtained by methods known in the art. The ouabain-resistant $Na^+$—$K^+$-ATPase can be derived, isolated or obtained from various target cell types. Examples of target cell types include, but are not limited to, kidney, heart, pineal gland, skeletal muscle, retina horizontal, retina Muller cells, brain cortical astrocytes, cerebellar granule neurons, cortical neurons and Hippocampal neurons. In a specific embodiment, the target cells are derived, isolated or obtained from a patient exhibiting a disease state that is related to the dysfunction of the ouabain-resistant $Na^+$—$K^+$-ATPase (Decollogne et al., The Sodium Pump, Bamberg and Schoner (eds) pp. 812-815, 1994). Examples of the disease state include, but are not limited to, cardiac malfunctions such as congestive heart failure, paroxysmal atrial tachycardia or atrial fibrillation, edematous disorders such as congestive heart failure, cirrhosis of the liver and nephrotic syndrome, and hypotension. In a specific embodiment, the ouabain-resistant $Na^+$—$K^+$-ATPase is derived from a rodent, an amphibian or a butterfly species. For example, a suitable ouabain-resistant $Na^+$—$K^+$-ATPase can be derived from a mouse, a rat, a toad Bufo marinus or a Monarch butterfly Danaus plexippus. Alternatively, the ouabain-resistant $Na^+$—$K^+$-ATPase can be obtained by converting or mutating an ouabain-sensitive $Na^+$—$K^+$-ATPase into an ouabain-resistant one. The ouabain-resistant $Na^+$—$K^+$-ATPase can be obtained by changing or substituting one or both border amino acid residues of the H1-H2 extracellular domain of $\alpha$ subunit of an ouabain-sensitive $Na^+$—$K^+$-ATPase to a charged amino acid residue, including a positively or negatively charged amino acid. Additional examples of mutations that confer ouabain resistance to an otherwise ouabain-sensitive $Na^+$—$K^+$-ATPase is disclosed in Lingrel et al., The Sodium Pump (Bamberg and Schoner, Ed.) pp. 276-286, 1994, the content of which is incorporated herein by reference in its entirety. The nucleotide sequence for rat, butterfly Monarch Danaus plexippus and toad Bufo marinus $\alpha 1$ $Na^+$—$K^+$-ATPase is disclosed in Shull et al., Biochemistry 25:8125-8132, 1986; Jaisser et al., J. Biol. Chem. 267:16895-16903, 1992 and Holzinger et al., FEBS 314:477-480, 1992, respectively, the teachings of which are incorporated in their entirety herein by reference.

Cells of animal origin, particularly, rodent species such as mouse or rat, amphibians such as toad Bufo marinus and butterfly species such as Monarch butterfly Danaus plexippus can serve as a nucleic acid source for the isolation of a isoforms of $Na^+$—$K^+$-ATPase nucleic acids. The DNA can be obtained by standard procedures known in the art from cloned DNA (e.g., a DNA "library"), chemical synthesis, cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II; the entire teachings of which are incorporated in its entirety by reference herein). Clones derived from genomic DNA can contain regulatory and intron DNA regions in addition to coding regions; clones derived from cDNA or RNA contain exon sequences. Whatever the source, the gene is generally molecularly cloned into a suitable vector for propagation of the gene.

In the molecular cloning of the gene from cDNA, cDNA can be generated from totally cellular RNA or mRNA by methods that are known in the art. The gene can also be obtained from genomic DNA, where DNA fragments are generated (e.g. using restriction enzymes or by mechanical shearing), some of which will encode the desired gene. The linear DNA fragments can then be separated according to size by standard techniques, including but not limited to, agarose and polyacrylamide gel electrophoresis and column chromatography.

Once the DNA fragments are generated, identification of the specific DNA fragment containing all or a portion of the $Na^+$—$K^+$-ATPase gene can be accomplished in a number of ways known to those skilled in the art (Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II; Shilo and Weinberg, 1981, *Proc. Natl. Acad. Sci. USA* 78:6789-6792; the entire teachings of which are incorporated by reference herein in its entirety).

Ouabain-resistant $Na^+$—$K^+$-ATPase proteins and derivatives, analogs and fragments thereof can be obtained by methods known in the art, including but not limited to, recombinant expression methods, purification from natural sources, and chemical synthesis (Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II; Shilo and Weinberg, 1981, *Proc. Natl. Acad. Sci. USA* 78:6789-6792; the entire teachings of which are incorporated by reference herein in its entirety).

The test substance that is contacted with the ouabain-resistant $Na^+$—$K^+$-ATPase by the method of the invention can be a chemical compound, such as organic molecules, inorganic molecules, organic/inorganic molecules, proteins, peptides, polysaccharides, saccharides, glycoproteins, nucleic acid strands or oligonucleotides like deoxyribonucleic acid (hereinafter "DNA") and ribonucleic acid (hereinafter "RNA"), or mixture of compounds like in the case of a library of test substances, a natural extract or tissue culture extract, whose effect on an ouabain-resistant $Na^+$—$K^+$-ATPase is determined by one or more of the methods described herein. The test substance can be an organic molecule, such as a steroid, cardiac glycoside or structurally similar compound, or a combinatorial library of such compounds. Ouabain itself is not considered a "test substance" as that term is used herein.

Activity of an ouabain-resistant $Na^+$—$K^+$-ATPase is measured or detected by methods known in the art, which methods include, but are not limited to, coupled-enzyme assays (Haupert, G. et al., *Am. J. Physiol.*, 247:F919-F924, 1984), ATP hydrolysis assays (Doucet et al., *Am. J. Physiol.*, 237(2): F105-F113, 1979), and ion transport assays (Cantiello et al., *Am. J. Physiol.*, 255:F574-F580, 1988). The assay can be quantitative or qualitative.

The level of activity measured or detected for ouabain-resistant $Na^+$—$K^+$-ATPase, when contacted with the test substance, is compared to the ATPase activity in the presence of HIF under comparable conditions.

HIF is isolated from mammalian organs, tissues or cell types containing HIF. In a specific embodiment, the HIF is isolated from hypothalamus (e.g., bovine hypothalamus) according to the procedures disclosed in U.S. Pat. No. 5,716, 937 or Tymiak et al., *Proc. Natl. Acad. Sci. USA* 90:8189-8193, 1993; the teachings of which are incorporated herein by reference in their entirety.

HIF generally is attributed with having the following characteristics: 1) it is a regio-chemical or stereo-chemical isomer of ouabain; 2) it specifically and reversibly binds ouabain-resistant $Na^+$—$K^+$-ATPase; and 3) after naphtholylation, it yields a CD spectrum substantially different from that of ouabain, see U.S. Pat. No. 5,716,937. It should be recognized that an HIF analogue, derivative, solvate or related compound having HIF inhibitory activity on an ouabain-resistant $Na^+$—$K^+$-ATPase can also be used, although it is ideal that HIF itself is used.

"Comparable conditions" according to the method of the invention are defined as the conditions of an assay conducted in substantially the same manner as a referent assay. That is to say, if an assay is to be the object of comparison (i.e., if a comparison of activity of the test substance is to be made to the activity of a reference compound such as HIF), then the assay of activity of the reference material would be the referent assay under conditions equivalent to, or the same as, conditions under which the activity of the test substance was assayed. The concentration(s) of the test substance used in methods described herein generally are equivalent or the same as that of the HIF. In comparing the activity of the test substance with that of HIF, a determination is made as to whether the test substance inhibits the activity of the same ouabain-resistant $Na^+$—$K^+$-ATPase (e.g., rat kidney) to the same extent as HIF inhibitory activity.

"HIF inhibitory activity" is defined herein to mean the inhibition of the ouabain-resistant $Na^+$—$K^+$-ATPase exhibited by HIF. For example, a test substance can be determined to have HIF inhibitory activity if it inhibits the same ouabain-resistant $Na^+$—$K^+$-ATPase (e.g., rat kidney) to the equivalent or same degree as HIF at the equivalent or same concentration and under equivalent or the same conditions under which HIF exhibits inhibitory activity. In one embodiment, a positive result is found when the level of ouabain-resistant $Na^+$—$K^+$-ATPase activity measured when the ouabain-resistant $Na^+$—$K^+$-ATPase is contacted with the test substance is the same as or less than that measured when the ouabain-resistant $Na^+$—$K^+$-ATPase is contacted with HIF under comparable conditions. A test substance that would be of particular interest can be one that exhibits, for example, from about the same to about ten times the HIF inhibitory activity.

In comparing the activity of an ouabain-resistant $Na^+$—$K^+$-ATPase (or "pump") measured when the pump is contacted with a test substance with that when the pump is contacted with HIF, it is unnecessary to measure the activity of the ouabain-resistant $Na^+$—$K^+$-ATPase in parallel, although such parallel measurement is considered to be within the scope of the invention.

In another embodiment, ouabain-resistant $Na^+$—$K^+$-ATPase inhibitory activity can be measured or detected using a coupled-assay, wherein the ouabain-resistant $Na^+$—$K^+$-ATPase is contacted with a test substance in the presence of ATP and a non-ATP substrate. More specifically, a test substance is preincubated in a buffer containing ouabain-resistant $Na^+$—$K^+$-ATPase and ATP. The preincubation is carried out in the presence of chelators such as norepinephrine, BSA, and EGTA to avoid interferences by ionic species present in the enzyme or HIF fractions, such as vanadate, free fatty acids, and bivalent cations. After preincubation, the incubating solution is added to a prewarmed reading solution containing buffering agents (physiological pH is used), ATP, and a non-ATP substrate, such as NADH. The enzymatic reaction is conducted at a temperature where the enzyme is active, e.g. from about 25° C. to about 40° C. for a period of time where activity, if present, is detected for about 1 second to about 5 minutes or more. A more detailed description of this assay can be found in Haupert, G., et al., *Am. J. Physiol.*, 247:F919-F924, 1984; the teachings of which are incorporated by reference in their entirety.

In one embodiment, the non-ATP substrate is NADH which is oxidized to form $NAD^+$. The oxidation of the non-ATP substrate and, thus, enzyme activity, is measured either by an increase of the amount (or accumulation) of the oxidized substrate, or a decrease of the amount (or depletion) of the non-ATP substrate. The oxidation reaction is monitored constantly, intermittently or finally by techniques known in the art. For example, spectrophotometry can detect a decrease of the amount of the non-ATP substrate or an increase of the amount of the oxidized non-ATP substrate. The enzymatic activity can be calculated from the slope of the oxidation reaction. Enzymatic activity typically is expressed as µmol (of the decrease of the non-ATP substrate or the increase of the oxidized form of the non-ATP substrate)/µg protein/min. In one particular embodiment, the inhibitory activity of the test substance is expressed as percent of the control sample assay, where the control sample assay is performed under the same conditions but in the absence of either the test substance or HIF. In one embodiment, the conversion of NADH to $NAD^+$ is measured by a decrease of the amount of the NADH. In another embodiment, the decrease of the amount of the NADH is measured by a decrease in absorbance at 340 nm. An example of a suitable assay employing NADH can be found in Haupert, G., et al., *Am. J. Physiol.*, 247:F919-F924, 1984; the teachings of which are incorporated in their entirety.

A comparison is then made between the measurement, or detection, of oxidation of the non-ATP substrate when the ouabain-resistant $Na^+$—$K^+$-ATPase is in the presence of the test substance with the measurement, or detection, of oxidation of the non-ATP substrate when the ouabain-resistant $Na^+$—$K^+$-ATPase is in the presence of HIF, thereby determining whether the test substance exhibits HIF inhibitory activity.

In another embodiment, the ouabain-resistant $Na^+$—$K^+$-ATPase is contacted with a test substance in the presence of ATP, wherein the terminal phosphate group ($P_3$) is labeled. The $P_3$ of ATP is labeled in such a way that the label does not substantially interfere with the hydrolysis of ATP by the ouabain-resistant $Na^+$—$K^+$-ATPase. The label of the $P_3$ is selected from, for example, the group consisting of a radiolabel, a fluorescent label, a luminescent label and an enzymatic label. In one embodiment, the labeled ATP is $[^{32}P]$ATP.

In this embodiment, ouabain-resistant $Na^+$—$K^+$-ATPase activity can be measured by an ATP hydrolysis assay. Typically, a suitable ATP hydrolysis assay includes preincubating a test substance in a physiological buffer containing isolated ouabain-resistant $Na^+$—$K^+$-ATPase. Parallel experiments can be carried out in the presence of different buffer solutions or chelators during preincubation, such as norepinephrine, EDTA, EGTA, glutathione, mercaptoethanol, and BSA, to evaluate the ionic requirements for the binding of the test substance, and to determine if, in comparison to HIF, chelators interfere with the inhibitory activity of the test substance. After the preincubation period, the incubation solution containing ATP (in which $P_3$ is labeled) is allowed to proceed for a sufficient time to cleave labeled $P_3$ from $[^{32}P]$ATP at a temperature, for example, in a range from about 25° C. to about 37° C., and from about 2 to 30 minutes. The reaction is then terminated by, for example, the addition of perchloric acid, or some other suitable method.

The liberated, labeled $P_3$ is then separated from the rest of the reaction mixture by a suitable separation technique, such as is known in the art. In one embodiment, the liberated labeled $P_3$ is separated from the rest of the reaction mixture by centrifugation. In a specific embodiment, the liberated labeled $P_3$ is separated from the rest of the reaction mixture by centrifugation in the presence of activated charcoal.

The amount of the liberated labeled $P_3$ is measured.

The amount of the liberated $^{32}P$ (or the amount of $[^{32}P]$ATP remaining) can be measured by, for example, liquid scintillation counting. The inhibitory activity of the test substance and HIF is expressed as percent of the control sample; that is, the assay can be performed in the absence of either the test substance or HIF.

A comparison is then made between the ouabain-resistant $Na^+$—$K^+$-ATPase activity in presence of the test substance with that of the ATPase activity incubating in the presence of HIF under comparable conditions. The comparison of activity between the two conditions is through the measurement or detection of liberated labeled $P_3$.

In another embodiment of the present invention, isotopic $Rb^+$ is used in screening a test substance for HIF inhibitory activity. A screening method is used to examine the putative inhibitory effect of a test substance upon the ouabain-resistant $Na^+$—$K^+$-ATPase by analyzing the uptake of the isotopic $Rb^+$ into, for example, reconstituted liposomes containing, or cells expressing or containing, the ouabain-resistant $Na^+$—$K^+$-ATPase. Examples of $^{86}Rb^+$-containing compounds include, but are not limited to, $Rb^+$ salts, such as RbCl, RbBr and RbAc. In a specific embodiment, the isotopic $Rb^+$ is $^{86}Rb^+$. An example of a suitable assay employing isotopic $Rb^+$ is described in Anner et al., *Am. J. Physiol.*, 258:F144-F153, 1990; the teachings of which are incorporated by reference in their entirety.

Purified ouabain-resistant $Na^+$—$K^+$-ATPase can be reconstituted into phosphatidylcholine liposomes using methods in the art, such as the cholate-dialysis method disclosed by Anner and Moosmayer in *Biophys. Res. Commun.* 129:102-108, 1985. Cells containing ouabain-resistant $Na^+$—$K^+$-ATPase, such as rat kidney cells, can be prepared by standard techniques known in the art (see, for example, Shyjan and Levenson, *Biochemistry* 28:4531-4535, 1989; the entire teachings of which are incorporated by reference). To measure ion transport activity of the reconstituted liposomes containing, or cells containing or expressing, ouabain-resistant $Na^+$—$K^+$-ATPase, freshly reconstituted liposomes or isolated cells are washed with a physiological solution and resuspended. A test substance is preincubated with the washed reconstituted liposomes or cells. After preincubation, a compound containing an isotopic Rb, such as $^{86}RbCl$, is added. The incubation is stopped after sufficient time, form about 1 to 5 minutes at about 25° C. to about 37° C., to allow internal accumulation of $^{86}Rb^+$. The liposomes or cells are separated from the medium and the amount of isotopic $Rb^+$ present in the liposomes or cells are counted. The inhibitory activity of the test substance and HIF is expressed as percent of the control sample, carried out in the absence of the test substance and HIF.

$Rb^+$ present in liposomes containing, or in the cells expressing or containing, the ouabain-resistant $Na^+$—$K^+$-ATPase is separated from the unincorporated or liberated compound containing $Rb^+$ by a suitable separation technique, such as is known in the art. In one embodiment, the $Rb^+$ present in the cells is separated from the unincorporated or liberated compound containing $Rb^+$ by centrifugation through, for example, an oil layer, such as a phthalate oil layer. In another embodiment, the $Rb^+$ present in the liposomes is separated from the unincorporated or liberated compound containing $Rb^+$ by chromatography. In one embodiment, the amount of the $^{86}Rb^+$ present in the liposomes or the cells is measured by a gamma counter.

A comparison is then made between the ouabain-resistant $Na^+$—$K^+$-ATPase activity incubated in presence of the test substance with that of the ATPase activity incubated in the presence of HIF under comparable conditions. The comparison of activity between the enzyme being incubated with the test substance versus HIF is made through the measurement or detection of $^{86}Rb^+$ present in the liposomes or cells expressing or containing ouabain-resistant $Na^+$—$K^+$-ATPase.

Inhibitors of an ouabain-resistant $Na^+$—$K^+$-ATPase identified by the screening methods disclosed above can be employed to treat or prevent certain diseases or disorders, such as a cardiac malfunction, to produce a positive inotropic effect. Examples of disorders or diseases that can be treated by test substances identified by the method of the invention are taught in U.S. Pat. No. 5,716,937, the entire content of which is incorporated herein by reference. U.S. Pat. No. 5,716,937 discloses methods of treating cardiac malfunction such as congestive heart failure, paroxysmal atrial tachycardia and atrial fibrillation, edematous disorders such as congestive heart failure, cirrhosis of the liver or nephrotic syndrome and hypotension, by administering a positive inotropic effect-producing glycosidic HIF. The inhibitors identified by the invention can be isolated and/or prepared and incorporated into suitable pharmaceutical compositions by suitable methods, such as those known in the art, for oral, parenteral (or intravenous) delivery.

The present invention also includes kits which can be employed using the methods disclosed herein. In specific embodiments, kits of the invention can include all or some of the following items: (a) an isolated ouabain-resistant $Na^+$—$K^+$-ATPase and/or reconstituted liposomes containing or cells containing or expressing an ouabain-resistant $Na^+$—$K^+$-ATPase; (b) HIF; (c) a non-ATP substrate, such as NADH; (d) ATP and/or labeled ATP; and (e) a compound containing isotopic $Rb^+$.

The following are examples of specific embodiments of the invention described herein. They are intended to serve as illustrations and not limitations of the present invention.

EXEMPLIFICATION

Example 1

Coupled-Enzyme Assay $Na^+$—$K^+$-ATPase activity is measured spectrophotometrically at about 37° C. as a decrease in absorbance at 340 nm due to of the oxidation of NADH, as previously described (Haupert et al., *Am. J. Physiol.* 247:F919-F924, 1984).

The test substance and HIF, typically in amounts of nanograms or micrograms, are each individually preincubated with 0.5 μg of purified $Na^+$—$K^+$-ATPase at about 37° C. for about 30 minutes in a final volume of 50 μl of preincubation mixture containing 100 mM NaCl, 3 mM $MgCl_2$, 50 mM tris(hydroxymethyl)aminomethane (Tris).HCl, pH 7.4. The inhibitory activity of the test substance and HIF is measured in the presence, during preincubation, of the following chelators: 2 mM norepinephrine, 2 mg/ml BSA, and 1 mM ethylene glycol-bis (β-aminoethyl ether)-N,N,N',N'-tetraacetic acid (EGTA) to avoid interferences by vanadate, liberated fatty acids, and bivalent cations (Carilli et al., *J. Biol. Chem.* 260:1027-1031, 1985). After preincubation, 40 μl of the incubating solution are added to 1 ml of the prewarmed reading solution: 100 mM NaCl, 25 mM KCl, 6 mM $MgCl_2$, 1.4 mM phosphoenolpyruvate, 1 mM dithiothreitol, 20 mM N-2-hydroxyethylpiperazine-N'-2-ethanesulfonic acid (HEPES), 3 mM ATP, 0.26 mM NADH, 10 μg/ml lactate dehydrogenase, and the absorbance is recorded at about 37° C. for at least 2 minutes. The inhibitory activity of the test substance and HIF is expressed as percent of the control sample, carried out in the same conditions but in the absence of the test substance and HIF.

Example 2

ATP Hydrolysis Assay $Na^+$—$K^+$-ATPase activity is assayed detecting or measuring the release of $^{32}P$ from $[^{32}P]ATP$, as previously described (Doucet et al., *Am. J. Physiol.* 237:F105-F113, 1979). Test substance and HIF, typically in amounts of nanograms or micrograms, are each individually preincubated with 0.3 μg of purified enzyme for 45 minutes at about 37° C. in 50 μl final volume of preincubation medium containing 140 mM NaCl, 3 mM $MgCl_2$, 50 mM HEPES-Tis, pH 7.4. Parallel experiments are carried out, when specified, in the presence of different buffer solutions or chelators during preincubation, such as 2 mM norepinephrine, 1 mM EDTA, 1 mM EGTA, 1 mM glutathione, 5 mM mercaptoethanol and 2 mg/ml BSA, to evaluate the ionic requirements for the binding of the test substance, and to find out if, in comparison to HIF, chelators interfere with the inhibitory activity of the test substance. After the preincubation period, 10 μl of incubation solution, containing 10 mM KCl and 20 nCi $[^{32}P]ATP$ (0.5-3 Ci/mmol) are added, and the reaction is continued for about 15 minutes at about 37° C. The reaction is stopped by acidification with ice-cold perchloric acid solution at 30% vol/vol. $^{32}P$ is separated by centrifugation with activated charcoal, and radioactivity is measured by liquid scintillation counting (Beckman LS 5000 CE). The inhibitory activity of the test substance and HIF is expressed as percent of the control sample, carried out in the absence of the test substance and HIF.

Example 3

Ion Transport Assay

Purified $Na^+$—$K^+$-ATPase is reconstituted into phosphatidylcholine liposomes using the cholate-dialysis method disclosed by Anner and Moosmayer in *Biophys. Res. Commun.* 129:102-108, 1985. Cells containing an ouabain-resistant $Na^+$—$K^+$-ATPase, such as rat kidney cells or rat blood cells (erythrocytes) are prepared by the standard techniques known in the art (Shyjan and Levenson, *Biochemistry* 28:4531-4535, 1989; Carilli et al., *J. Biol. Chem.*, 260:1027-1031, 1985).

Ion transport activity of the reconstituted liposomes containing an ouabain-resistant $Na^+$—$K^+$-ATPase, isolated kidney cells, or erythrocytes, which contain α1/β1 complex as the sole $Na^+$—$K^+$-ATPase, is assayed by previously described methods (Anner, et al., *Am. J Physiol.*, 258:F144-F153, 1990; Cantiello, et al., *Am. J. Physiol.*, 255:F574-F580, 1988; Crabos, et al., *Am. J. Physiol.*, 254:F912-F917, 1988, respectively). Freshly reconstituted liposomes, isolated kidney cells or erythrocytes are washed with a physiological solution containing 140 mM NaCl, 1 mM $CaCl_2$, 1 mM $MgSO_4$, 20 mM HEPES, 5 mM $Na_2HPO_4$ and 10 mM glucose, pH 7.5, and resuspended (Anner et al., *Am. J. Physiol.* 258:F144-F153, 1990).

The test substance and HIF, typically in amounts of nanograms or micrograms, are each individually preincubated from about 30 minutes to about 3 hours at about 0° C. (liposomes), about 37° C. (kidney cells or erythrocytes) with washed reconstituted liposomes, kidney cells or erythrocytes in a final volume of 2.5 μl (liposomes) 50 μl (kidney cells, erythrocytes, 25% final hematocrit in the case of erythrocytes). The preincubation is carried out both in the presence and absence of 5 mM KCl. After this period, 0.3 μCi $^{86}RbCl$ (1.5 μCi/ml) and 5 mM KCl (when not present in the preincubation) are added. The incubation is stopped after 30 minutes by adding 100 to 500 μl ice-cold physiological buffer solution. Parallel experiments are conducted in the absence of either the test substance or HIF, but in the presence of $10^{-2}$ M ouabain to allow determination of ion ($Rb^+$) transport activity not related to the ouabain-resistant $Na^+$—$K^+$-ATPase. The liposomes are separated by chromatography. The kidney cells or erythrocytes are separated from the medium by rapid centrifugation through a 500 µl phthalate oil layer, after which the tips of the tubes are sliced off and counted for $^{86}Rb$ content (Beckman gamma counter 5500 B). The ouabain-sensitive $^{86}Rb$ uptake is calculated as the difference between the Rb uptake in the absence and presence of $10^{-2}$ M ouabain.

While this invention has been particularly shown and described with references to preferred embodiments thereof, it will be understood by those skilled in the art that various changes in form and details may be made therein without departing from the scope of the invention encompassed by the appended claims.

What is claimed is:

1. An assay for screening a test substance for hypothalamic inhibitory factor (HIF) inhibitory activity of an ouabain-resistant $Na^+$—$K^+$-ATPase, comprising the steps of:
   (a) contacting liposomes containing, or cells expressing or containing, the ouabain-resistant $Na^+$—$K^+$-ATPase with the test substance in the presence of a compound comprising isotopic $Rb^+$, under suitable conditions for isotopic $Rb^+$ uptake by the liposomes or the cells;
   (b) measuring or detecting the amount of the isotopic $Rb^+$ present in the liposomes or the cells; and
   (c) comparing the amount of the isotopic $Rb^+$ present in the liposomes or cells measured or detected in step (b) with a measured or detected amount of isotopic $Rb^+$ obtained by contacting liposomes containing, or cells containing or expressing, ouabain-resistant $Na^+$—$K^+$-ATPase with HIF in the presence of the compound comprising isotopic $Rb^+$ under comparable conditions, thereby determining whether the test substance exhibits HIF inhibitory activity.

2. The method of claim 1, further comprising the step of contacting ouabain-resistant $Na^+$—$K^+$-ATPase with HIF under suitable conditions in an aqueous medium for ouabain-resistant $Na^+$—$K^+$-ATPase activity, wherein said activity is measured or detected, thereby providing the measurement or detection to be compared with the test substance.

3. The method of claim 1, wherein the ouabain-resistant $Na^+$—$K^+$-ATPase is obtained by substituting one or both border amino acid residues of the H1-H2 extracellular domain of α subunit of an ouabain-sensitive $Na^+$—$K^+$-ATPase with a charged amino acid residue.

4. The method of claim 1, wherein the isotopic $Rb^+$ is $^{86}Rb^+$.

5. The method of claim 4, wherein the amount of $^{86}Rb^+$ present in the liposomes or the cells containing the ouabain-resistant $Na^+$—$K^+$-ATPase is measured by a gamma counter.

6. The method of claim 1, wherein the isotopic $Rb^+$ present in the liposomes containing the ouabain-resistant $Na^+$—$K^+$-ATPase is separated from the unincorporated or liberated compound comprising isotopic $Rb^+$ by chromatography.

7. The method of claim 1, wherein the isotopic $Rb^+$ present in the cells containing the ouabain-resistant $Na^+$—$K^+$-ATPase is separated from the unincorporated or liberated compound comprising isotopic $Rb^+$ by centrifugation through an oil layer.

8. The method of claim 7, wherein the oil layer is a phthalate oil layer.

9. The method of claim 1, wherein the ouabain-resistant $Na^+$—$K^+$-ATPase is isolated from a target cell.

10. The method of claim 9, wherein the target cell is selected from the group consisting of a kidney cell, a heart cell, a pineal gland cell, a skeletal muscle cell, a retina horizontal cell, a retina Muller cell, a brain cortical astrocyte, a cerebellar granule neuron, a cortical neuron and a Hippocampal neuron.

11. The method of claim 1, wherein the ouabain-resistant $Na^+$—$K^+$-ATPase is selected from the group consisting of a rodent, toad and butterfly ÿ1 $Na^+$—$K^+$-ATPase.

12. The method of claim 11, wherein the ouabain-resistant $Na^+$—$K^+$-ATPase is a rat kidney α1 ouabain-resistant $Na^+$—$K^+$-ATPase.

13. The method of claim 11, wherein the ouabain-resistant $Na^+$—$K^+$-ATPase is a *Bufo marinus* α1 ouabain-resistant $Na^+$—$K^+$-ATPase.

14. The method of claim 11, wherein the ouabain-resistant $Na^+$—$K^+$-ATPase is a *Danaus plexippus* α1 $Na^+$—$K^+$-ATPase.

15. The method of claim 1, wherein the HIF is isolated from bovine hypothalamus.

16. A kit, comprising:
   (a) reconstituted liposomes containing, or cells containing or expressing, an ouabain-resistant $Na^+$—$K^+$-ATPase;
   (b) a compound containing isotopic $Rb^+$ and
   (c) hypothalamic inhibitory factor (HIF) HIF.

* * * * *